(12) United States Patent
Thacker et al.

(10) Patent No.: US 8,301,248 B1
(45) Date of Patent: Oct. 30, 2012

(54) SEQUENCED AND SIMULTANEOUS STIMULATION FOR TREATING CONGESTIVE HEART FAILURE

(75) Inventors: James R. Thacker, Eureka, MO (US); Kelly H. McClure, Simi Valley, CA (US); Todd K. Whitehurst, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 529 days.

(21) Appl. No.: 12/163,803

(22) Filed: Jun. 27, 2008

Related U.S. Application Data

(63) Continuation of application No. 10/383,213, filed on Mar. 6, 2003, now abandoned.

(60) Provisional application No. 60/362,421, filed on Mar. 6, 2002.

(51) Int. Cl.
*A61N 1/36* (2006.01)

(52) U.S. Cl. ........... 607/9; 607/1; 607/2; 607/4; 607/11; 607/27; 607/28; 607/66; 607/67; 607/74; 607/75

(58) Field of Classification Search .................. 607/1–2, 607/4, 9, 11, 27–28, 66–67, 74–75
See application file for complete search history.

(56) References Cited

U.S. PATENT DOCUMENTS

| | | |
|---|---|---|
| 3,769,986 A | 11/1973 | Herrmann |
| 3,835,864 A | 9/1974 | Rasor et al. |
| 3,943,936 A | 3/1976 | Rasor et al. |
| 4,444,195 A | 4/1984 | Gold |
| 4,848,352 A | 7/1989 | Pohndorf et al. |
| 4,856,525 A | 8/1989 | van den Honert |
| 4,949,720 A | 8/1990 | Thompson |
| 5,184,616 A | 2/1993 | Weiss |
| 5,193,539 A | 3/1993 | Schulman et al. |
| 5,300,107 A | 4/1994 | Stokes et al. |
| 5,324,316 A | 6/1994 | Schulman et al. |
| 5,411,535 A | 5/1995 | Fujii et al. |
| 5,431,681 A | 7/1995 | Helland |
| 5,476,502 A | 12/1995 | Rubin |

(Continued)

FOREIGN PATENT DOCUMENTS

EP 1809372 A1 7/2007

(Continued)

OTHER PUBLICATIONS

"U.S. Appl. No. 10/383,213, Amendment A and Response filed Jun. 27, 2006 to Non-Final Office Action mailed Feb. 27, 2006", 12 pgs.

(Continued)

*Primary Examiner* — Carl H Layno
*Assistant Examiner* — Deborah Malamud
(74) *Attorney, Agent, or Firm* — Schwegman Lundberg & Woessner, P.A.

(57) ABSTRACT

A patient's ejection fraction is maximized through simultaneous sensing and stimulating across multiple electrodes. In one exemplary embodiment, a catheter or lead having multiple electrodes connected to a pulse generator is used. The pulse generator provides individual current control of the stimulus applied to each electrode, and further includes the ability to sense intrinsic and evoked depolarization through multiple electrodes. In another exemplary embodiment, a multiplicity of individual implantable microstimulators, each having its own current source and/or sensor and electrodes, cooperate in concert to provide multi-site stimulation and sensing.

8 Claims, 5 Drawing Sheets

U.S. PATENT DOCUMENTS

| | | |
|---|---|---|
| 5,549,109 A | 8/1996 | Samson et al. |
| 5,800,465 A | 9/1998 | Thompson et al. |
| 5,800,471 A | 9/1998 | Baumann |
| 5,814,089 A | 9/1998 | Stokes et al. |
| 5,941,906 A * | 8/1999 | Barreras et al. .......... 607/66 |
| 6,052,615 A | 4/2000 | Feild et al. |
| 6,076,014 A | 6/2000 | Alt |
| 6,081,748 A | 6/2000 | Struble et al. |
| 6,096,064 A | 8/2000 | Routh |
| 6,122,545 A | 9/2000 | Struble et al. |
| 6,141,588 A | 10/2000 | Cox et al. |
| 6,181,969 B1 | 1/2001 | Gord |
| 6,266,567 B1 | 7/2001 | Ishikawa et al. |
| 6,409,674 B1 | 6/2002 | Brockway et al. |
| 6,757,970 B1 | 7/2004 | Kuzma et al. |
| 6,783,499 B2 | 8/2004 | Schwartz |
| 6,907,285 B2 | 6/2005 | Denker et al. |
| 7,003,350 B2 | 2/2006 | Denker et al. |
| 7,532,933 B2 | 5/2009 | Hastings et al. |
| 2002/0183791 A1 | 12/2002 | Denker et al. |
| 2002/0198604 A1 | 12/2002 | Schulman et al. |
| 2003/0032997 A1 | 2/2003 | Pianca et al. |
| 2003/0105505 A1 | 6/2003 | Pianca |
| 2004/0103906 A1 | 6/2004 | Schulman et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0219590 A1 | 9/2007 | Hastings et al. |
| 2007/0239248 A1 | 10/2007 | Hastings et al. |
| 2008/0021505 A1 | 1/2008 | Hastings et al. |
| 2008/0021532 A1 | 1/2008 | Kveen et al. |
| 2008/0109054 A1 | 5/2008 | Hastings et al. |

FOREIGN PATENT DOCUMENTS

| | | |
|---|---|---|
| EP | 1812104 A1 | 8/2007 |
| EP | 1835962 A1 | 9/2007 |
| WO | WO-00/00251 A1 | 1/2000 |
| WO | WO-02/09808 A1 | 2/2002 |
| WO | WO-2006045073 A1 | 4/2006 |
| WO | WO-2006045074 A2 | 4/2006 |
| WO | WO-2006045075 A1 | 4/2006 |
| WO | WO-2007067231 A1 | 6/2007 |
| WO | WO-2007067253 A1 | 6/2007 |
| WO | WO-2007115044 A2 | 10/2007 |
| WO | WO-2008011626 A1 | 1/2008 |

OTHER PUBLICATIONS

"U.S. Appl. No. 10/383,213, Amendment B and Response filed Dec. 8, 2006 Non-Final Office Action mailed Sep. 12, 2006", 10 pgs.

"U.S. Appl. No. 10/383,213, Amendment C and Response filed Aug. 29, 2007 to Non-Final Office Action mailed Mar. 8, 2007", 10 pgs.

"U.S. Appl. No. 10/383,213, Final Office Action mailed Jan. 31, 2008", 6 pgs.

"U.S. Appl. No. 10/383,213, Non-Final Office Action mailed Feb. 27, 2006", 9 pgs.

"U.S. Appl. No. 10/383,213, Non-Final Office Action mailed Mar. 8, 2007", 10 pgs.

"U.S. Appl. No. 10/383,213, Non-Final Office Action mailed Sep. 12, 2006", 11 pgs.

"U.S. Appl. No. 10/383,213, Response filed Nov. 29, 2007 to Restriction Requirement mailed Oct. 29, 2007", 5 pgs.

"U.S. Appl. No. 10/383,213, Restriction Requirement mailed Oct. 29, 2007", 6 pgs.

Cazeau, S., et al., "Première expérience de traitement de l'insuffisance cardiaque terminale par la stimulation multisite [First Experience in the Treatment of Terminal Cardiac Insufficiency by Multi-site Pacing]", (w/ English Summary at p. 2074), *Bull. Acad. Natle. Méd.*, 180(9), (1996), 2065-2078.

* cited by examiner

SEQUENCED AND SIMULTANEOUS STIMULATION FOR TREATING CONGESTIVE HEART FAILURE

The present application claims the benefit of U.S. patent application Ser. No. 10/383,213, filed Mar. 6, 2003, now abandoned, and U.S. Provisional Application Ser. No. 60/362,421, filed 6 Mar. 2002, which applications are incorporated herein by reference in their entirety.

BACKGROUND OF THE INVENTION

The present invention relates to implantable medical devices, and more particularly to an implantable pulse generator and sensor, e.g., an implantable pacemaker, that senses and stimulates cardiac tissue to treat congestive heart failure (CHF).

Congestive Heart Failure (CHF) is characterized by the left, right or both ventricles losing their ability to adequately pump blood to the lungs or body. Both Systolic and Diastolic CHF may be experienced, with Systolic CHF being the more common. Systole is the contraction of the heart by which the blood is forced onward and the circulation kept up. Thus, systolic pressure is the highest arterial blood pressure of a cardiac cycle and it occurs immediately after systole of the left ventricle of the heart. In contrast, diastole is the passive rhythmical expansion or dilation of the cavities of the heart during which they fill with blood. Hence, diastolic pressure is the lowest arterial blood pressure of a cardiac cycle occurring during diastole of the heart.

The recognized medical treatment today for CHF is a pharmacological solution, e.g., Beta blockers, diuretics and/or inotropic drugs. This treatment regime does not cure the underlying substrate or eliminate the symptoms. It does, however, help mitigate the symptoms and improve the patient's quality of life on a temporary basis.

Experimental approaches for dealing with CHF in the implantable pacemaker community have focused on increasing the efficiency of the contraction by coordinating the timing between the different chambers, and on the site of stimulation within each chamber. These approaches have included, for example, the following methods individually and in parallel: (i) 3-chamber pacing; (ii) 4-chamber pacing; (iii) left ventricular pacing by a coronary sinus lead, (iv) Bachman's Bundle pacing; and (v) RVOT pacing. All have met with limited success, but all are hampered by the lack of knowledge regarding the correct dynamic timing required during the sequencing of the chambers.

Consider the manner in which the heart naturally ejects and collects blood. During systole, the heart ejects a certain volume of blood V1 into the body's arterial system. During diastole, the heart collects another volume of blood V2 returning to the heart through the body's system of veins. Assuming that the body does not loose any significant amount of blood during this ejection and collection process, the volume of ejected blood V1 should be approximately equal to the volume of collected blood V2.

However, sometimes not all of the blood held in the ventricles of the heart is ejected during systole. That is, there may be a residual volume of blood, R, that remains in the heart after blood ejection during systole. (This residual volume, R, is also referred to as the "end systolic volume".) In the case of the left ventricle, which holds oxygen-rich blood that has returned from the lungs, any such residual volume of blood represents inefficient operation of the heart.

In the event that a residual volume of blood remains in the heart at the end of systole, when the blood returns to the heart during diastole, the volume of blood in the heart will have increased to a volume of V2+R, where V2 (the collected blood volume) is approximately equal to V1 (the ejected blood volume). The heart's natural solution to an inadequate ejection fraction (where "ejection fraction" is defined as the ejected blood volume V1 during systole divided by the total blood volume in the heart at the end of diastole, V2+R) is to make the next cardiac cycle's filling volume greater. That is, at the end of diastole, a greater volume of blood, V2+R, is in the heart, causing the heart to dilate (expand or stretch) to accommodate the increased blood volume. The increased blood volume in the heart is ejected during the next cycle, thereby providing a higher ejection fraction, and thereby self-correcting the inadequate ejection fraction. This natural self-correction is brought about by Starling's law.

Starling's law states that a muscle, including the heart muscle, responds to increased stretching at rest by an increased force of contraction when stimulated. Disadvantageously, however, there is a limit to Starling's law. That is, a point is soon reached where greater stretching does not produce a greater contraction. As a patient operates at the top of Starling's Curve, the myocardial tissue is being stretched and further dilated. This results in the growth of connective tissue within the myocardial tissue, which tissue growth hampers or hinders the muscle contraction. The stretching of the ventricles accelerates this connective tissue growth. Thus, a positive feedback loop is created moving the patient closer to a dangerous CHF situation. Additionally, the connective tissue also interferes with the conduction system of the heart, resulting in a slower, less forceful contraction. This condition may cause hyper or hypo myopathy.

Pacemakers known in the art provide monopolar or bipolar voltage stimulation, typically in the right atrium or the right ventricle. Some pacemakers and pacing leads further provide for voltage stimulation at multiple sites within the heart. See, e.g., U.S. Pat. Nos. 4,444,195; 4,848,352; 5,184,616; 5,476,502; 5,549,109; 5,800,471; 6,052,615; 6,076,014; 6,096,064; and 6,122,545.

It is a feature of the present invention to provide a more efficient and effective way to assist the heart to adequately perform its function as a pump.

SUMMARY OF THE INVENTION

The present invention addresses the above and other needs by providing a way to maximize the patient's ejection fraction. This is achieved by providing a means for simultaneously sensing and stimulating across multiple electrodes, thereby allowing for the critical timing and delivery of a created depolarization wave front that maximizes the ejection fraction.

The present invention includes a catheter, or lead, having multiple electrodes connected to a pulse generator. The pulse generator provides individual current control of the stimulus applied to each electrode, and further includes the ability to sense intrinsic and evoked depolarization through multiple electrodes. Thus, the invention provides simultaneous multi-site pacing and sensing, and is able, through appropriate sensing and timing of applied current stimuli to selected electrodes located at multiple sites in one or more heart chambers, e.g., in the left ventricle, to recreate a depolarization wave front that mimics a normal heart. Such depolarization wave front assists the heart so that the patient's ejection fraction may be maximized, thereby improving the patient's hemodynamics (where "hemodynamics", as used herein, is a broad term that relates to how efficiently the heart performs its function as a pump in delivering blood to the lungs and in delivering oxygen-filled blood from the left ventricle to tissue cells throughout the body).

Unlike pacemakers known in the art, which provide monopolar or bipolar voltage stimulation, and which do not allow for the effective stimulation of multiple electrodes, the present invention utilizes multiple electrodes through which current-controlled stimulation may be selectively provided, and wherein multiple electrodes are coupled to a means for sensing an intrinsic and/or evoked depolarization. With such configuration, the present invention is thus able to effectively sense the depolarization pattern occurring within a given heart chamber, e.g., the left ventricle, and on demand, or as programmed, provide selective current stimuli to electrodes spaced throughout the heart chamber so as to create or steer a depolarization wave front that mimics a normal heart, i.e., that maximizes stroke volume and reduces end systolic volume, thereby assisting the heart to perform its function of a pump more efficiently. Current-controlled pacing is superior to voltage-controlled pacing because it allows better fine tuning of the stimulus in the face of impedance variations, especially in light of tissue changes due to hypertension and chronic ischemia.

In accordance with one aspect of the invention, there is provided an implantable multi-channel stimulator, adapted to selectively provide current-controlled stimulation at multiple sites within a selected chamber or chambers of the heart, preferably including the left ventricle, in a controlled manner so as to fashion appropriate depolarization wave fronts to assist a diseased or malfunctioning heart to operate more efficiently as a pump.

In accordance with another aspect of the invention, current-controlled stimulation is simultaneously provided to multiple select stimulation sites.

It is thus a feature of the present invention to provide such an implantable multi-channel pacemaker that both senses cardiac activity and stimulates the cardiac tissue from a multi-channel, current-controlled pulse generator on demand as determined by the cardiac activity that is sensed, or as otherwise programmed.

It is a further feature of the invention to provide a method of treating congestive heart failure using a multi-channel current-controlled pulse generator coupled to multiple stimulation sites in the left ventricle, or other chambers of the heart, for the purpose of assisting the heart to operate more efficiently, i.e., to improve stroke volume and increase the ejection fraction.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The feasibility of multi-site pacing with purely hemodynamic intent has been demonstrated. See Cazeau, et al., "First Experience in the Treatment of Terminal Cardiac Insufficiency by Multi-site Pacing," Bull. Acad. Natle. Med., 1996, Vol. 180, No. 9, pp. 2065-2078 (Meeting of Dec. 3, 1996). Cazeau et al. report that the benefit in terms of quality of life obtainable from multi-site pacing seems to be connected with modifications of the left ventricular mechanics, which can also modify the volume of any possibly ventricular-atrial regurgitation. The Cazeau et al. reference indicates that it is essential to simplify the left ventricular probe implantation procedure in order to allow the dissemination and multi-center validation of the pacing technique. The present invention not only advantageously provides a simplified implantation procedure, but also provides a way to achieve multi-site pacing using a multi-channel current-controlled pulse generator in a way that achieves significant hemodynamic benefits for the patient, e.g., allows stimulation pulses to be delivered to the left ventricle so as to closely mimic the normal sequence of depolarization of the heart's chambers, maximizes stroke volume, and/or reduces end systolic volume.

Figure 1:
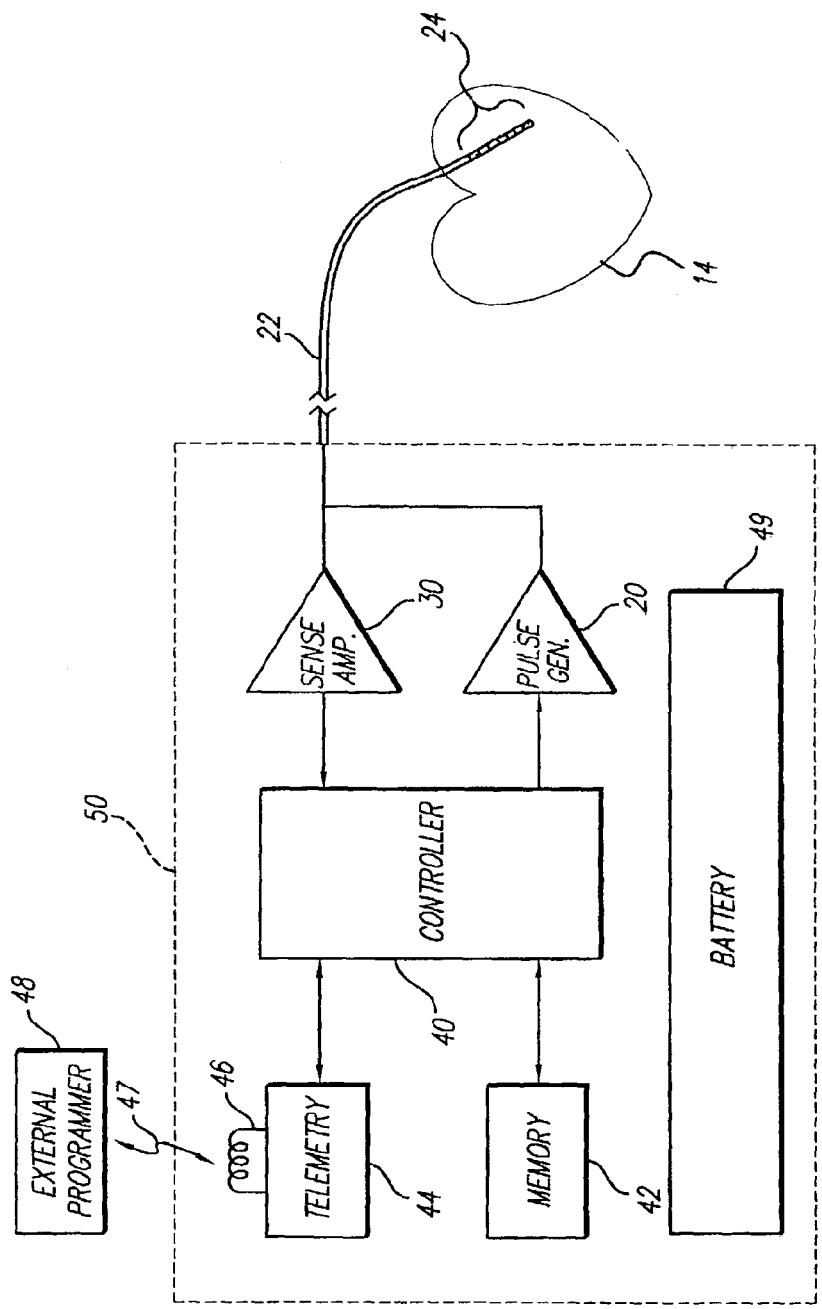
FIG. 1 is a functional block diagram of a multi-channel implantable pacemaker and multi-electrode catheter lead configured in accordance with the present invention.

As seen in FIG. 1, the present invention utilizes a pulse generator 20 adapted to be coupled to a patient's heart 14 through a suitable catheter or lead 22 having multiple electrodes 24 at or near its distal end. In a preferred embodiment, the lead 22 is inserted into the heart 14 so that its distal end, and at least some of the multiple electrodes 24, reside inside the left ventricle of the heart 14. It is to be emphasized that the invention is not limited to use only in the left ventricle, but left ventricle usage is the preferred site for achieving maximum hemodynamic benefits. Access to the left ventricle may be achieved through the Coronary Sinus and Great Vein. Access to the right atrium or right ventricle may be achieved as is known in the pacing art.

Also coupled to the multiple electrodes 24 through the lead 22 is a sense amplifier 30. The sense amplifier 30 is able to sense cardiac activity, e.g., intrinsic and/or evoked depolarization, as sensed at each of the locations where the individual electrodes 24 are located.

The pulse generator 20 and sense amplifier 30 are connected to a suitable controller 40, which may be a microprocessor or other control logic, e.g., state machine logic. The controller 40 is coupled to suitable memory circuitry 42 and telemetry circuitry 44.

All of the elements described thus far, e.g., the controller 40, memory 42, telemetry circuitry 44, pulse generator 20, and sense amplifier 30, along with a battery 49, are preferably housed in an hermetically-sealed case or housing 50, thereby allowing such elements to be implanted within the patient. When implanted, the lead 22 mechanically and electrically connects with the case 50, the sense amplifier 30, and pulse generator 20 through suitable feed-through terminals (not shown), as is known in the art. However, it is to be understood that the invention may also be practiced through use of a multi-channel current controlled stimulator whether the stimulator is implanted or not.

An antenna coil 46, connected to the telemetry circuitry 44, allows a telecommunicative link 47 (represented in FIG. 1 as a wavy arrow), e.g., an rf link, to be established between the telemetry circuitry 44 and an external programmer unit 48, also as is known in the art. Thus, when the unit 50 is implanted, the link 47 provides a mechanism for transferring programming and control signals to the controller 40 from the external programmer 48, and for transferring status and other signals to the external programmer 48 from the implanted device 50. The antenna coil 46, or a similar coil, may also be used to provide an inductive link with the implanted circuitry from an external source of power for the purpose of transferring energy (power) to the implanted unit 50 when, e.g., the battery 49 comprises a rechargeable battery, or other replenishable power source.

Figure 2:
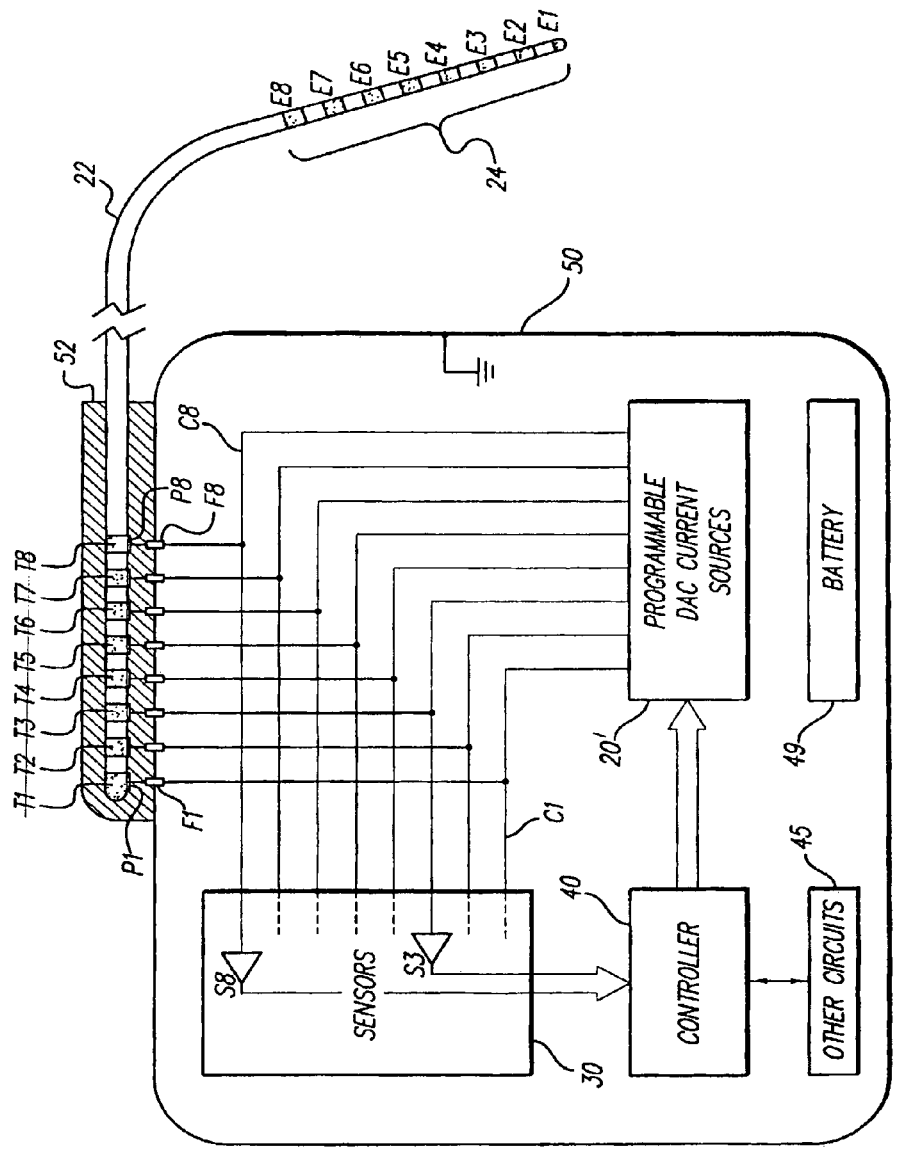
FIG. 2 is a functional block diagram that shows a preferred manner for achieving multi-channel current-controlled stimulation in accordance with the invention.

Turning next to FIG. 2, a functional block diagram is shown that depicts a preferred manner for providing current-controlled stimulation to the electrodes 24 in accordance with the present invention. The lead 22 shown in FIG. 2 has eight electrodes 24, labeled E1, E2, E3, . . . E8 at its distal end. A proximal end of the lead 22 similarly includes eight terminals T1, T2, T3, . . . T8. Individual wires embedded within the body of the lead 22 connect a respective one of the terminals T1, T2, T3, . . . T8 to a respective one of the electrodes E1, E2, E3, . . . E8. The use of eight electrodes and terminals on the lead 22 is only exemplary, as any suitable number of electrodes/terminals may be used, e.g., 4 to 16.

The lead 22, with multiple electrodes and terminals, may be fabricated using techniques as are known in the art, or as taught, e.g., in U.S. patent application Ser. No. 10/000,408, filed Nov. 2, 2001, now issued as U.S. Pat. No. 6,757,970; Ser. No. 10/188,424, filed Jul. 2, 2002, published as U.S. Patent Application Publication No. 2003/0032997A1 (now abandoned); and/or Ser. No. 10/305,924, filed Nov. 26, 2002, published as U.S. Patent Application Publication No. 2003/0105505A1 (now abandoned), which applications and patent are assigned to the same assignee as is the present application, and which applications and patent are incorporated herein by reference.

Still with reference to FIG. 2, the proximal end of the lead 22 is inserted into a header connector 52 mounted on the case 50 of the implantable device. When properly inserted into the connector 52, each terminal T1, T2, T3, . . . T8 makes electrical contact with respective pads P1-P8, which pads are connected through respective feed-through terminals F1-F8 to respective conductors C1-C8 inside the hermetically-sealed case 50.

Each of the conductors C1-C8 are connected to the sense amplifier 30 and programmable DAC (digital-to-analog) current sources 20'. The sense amplifier 30 includes respective sense amplifiers S1-S8 for sensing whatever signal is present on the respective conductor at the relevant sense time. Sensing may be done relative to a common ground reference, or relative to another conductor. That is, sensing may be conducted bipolarly between any two of the electrodes E1, E2, E3, . . . E8; or monopolarly between any electrode E1, E2, E3, . . . E8 and a common ground reference, such as the case 50; or through other electrode combinations.

Each of the conductors C1-C8 is likewise connected to the programmable DAC current sources 20'. Such current sources may be fabricated, as taught, e.g., in PCT Publications WO 00/00251, published 6 Jan. 2000; or WO 02/09808, published 7 Feb. 2002; or U.S. Pat. No. 6,181,969; which publications and patent are incorporated herein by reference. As taught in the cited references, each conductor C1-C8 is directly connected to its own programmable DAC current source, thereby avoiding the need for a multiplexer or other switch.

As further seen in FIG. 2, the sense amplifiers S1-S8, as well as the DAC current sources 20' are connected to the controller circuit 40, which in turn is connected to all the other circuits 45 contained within the unit 50.

It should be emphasized that the invention is not limited to the type of circuitry shown in FIG. 2. That is, the invention need not be limited to the use of programmable DAC current sources 20' within a single implantable housing 50, with each programmable DAC current source being coupled to the tissue to be stimulated through multiple electrodes E1, E2, . . . E8 carried on a single lead 22. Any type of implantable circuitry and/or lead configuration may be used to practice the invention so long as multiple stimulation and sensing sites are employed, and so long as the stimuli that are provided are current-controlled stimuli. As indicated previously, providing current-controlled stimuli is believed to be superior to providing voltage-controlled stimuli because current-controlled stimuli allow better fine-tuning of the stimuli in an environment of impedance variations, as occurs commonly within cardiac tissue. Thus, it is an important component of the invention to provide current-controlled stimuli, coupled with appropriate sensing, regardless of the type of implantable circuitry and electrode configurations used to provide such current-controlled pacing.

By way of example of alternate circuitry, reference is made to U.S. Patent Application Ser. No. 60/392,475, filed Jun. 28, 2002, which application is assigned to the same assignee as is the present application, and which application is incorporated herein by reference in its entirety. Such application, entitled "Battery-Powered Microstimulator and Method of Making Same" discloses a miniature single channel stimulator, referred to by its manufacturer, Advanced Bionics Corporation of Sylmar, Calif., as a BION® stimulator. Advantageously, the BION stimulator, due to its small size, may be easily implanted at a specific tissue or nerve site, e.g., through use of special, minimally-invasive implantation tools. The BION stimulator includes one or two electrodes on its case. Through such electrodes, electrical current stimuli may be applied to the tissue, and depolarization (or other) signals may be sensed. Due to its small size, it is possible to implant several such BION-type stimulators in close proximity to each other, and achieve the same type of current-controlled stimulation afforded by the circuitry, lead and electrodes shown in FIG. 2. Thus, it is seen that the present invention may be practiced using circuitry other than that shown in FIG. 2, e.g., using a multiplicity of such BION-type stimulators implanted in or near appropriate cardiac tissue, e.g., tissue of the left ventricle.

In operation, the controller circuit 40 of FIG. 2 monitors cardiac activity, e.g., depolarization signals, that are sensed through selected ones of the electrodes E1-E8. Depending upon what depolarization signals are sensed, or as otherwise programmed, the controller 40 steers the DAC current sources 20' to provide a current stimulus on selected ones on the electrodes E1-E8. The timing diagram of FIG. 3 is illustrative of how this may be done.

Figure 3:
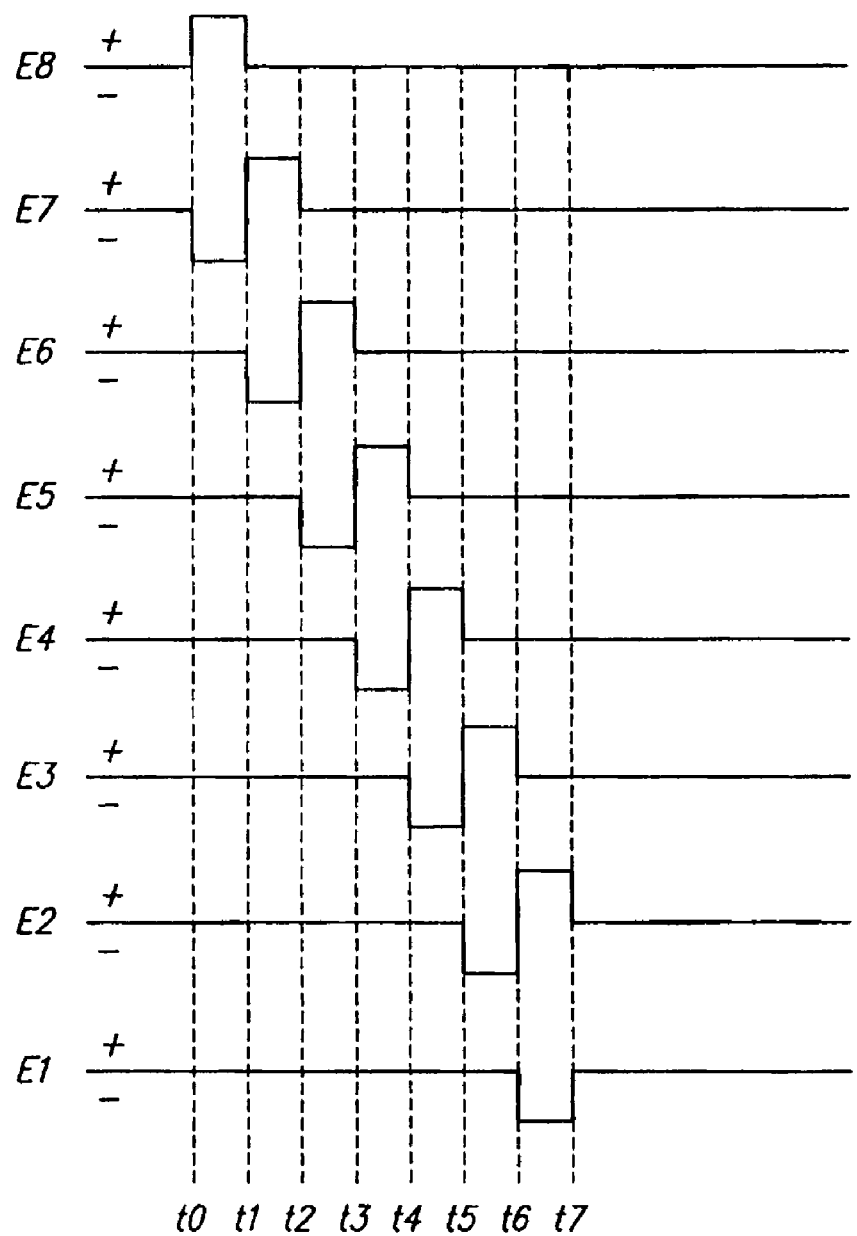
FIGS. 3-5 are timing waveform diagrams that illustrate examples of the operation of the invention used to create and steer depolarization wave fronts and (in the case of FIG. 5) sense cardiac activity.

As seen in FIG. 3, beginning at time t0, a positive current pulse appears on electrode E8 and a negative current pulse of the same amplitude appears on electrode E7. From a circuit point of view, this means that a current is being sourced or emitted from electrode E8 at the same time that a current of the same amplitude is being sunk into (received by) electrode E7. Thus, during the time t0-t1, electrode E8 operates as an anode (current source that generates a current +1) and electrode E7 operates as a cathode (current return path that generates a current −1). Stated differently, bipolar stimulation is provided between electrodes E8 and E7 with the direction of current flow being from E8 to E7.

Still with reference to FIG. 3, beginning at time t1 and continuing until time t2, electrode E7 sources a current of a fixed amplitude while electrode E6 simultaneously sinks a current of the same fixed amplitude. In other words, during the time t1-t2, a fixed current flows from electrode E7 to electrode E6. This process continues for each indicated time period. That is, beginning at time t2 and continuing until time t3, a fixed current flows from electrode E6 to electrode E5; for the time period t3-t4, a fixed current flows from electrode E5 to electrode E4; for the time period t4-t5, a fixed current flows from electrode E4 to electrode E3; for the time period t5-t6, a fixed current flows from electrode E3 to electrode E2; and for the time period t6-t7, a fixed current flows from electrode E2 to electrode E1. In this manner, assuming the electrodes E1-E8 are located within the ventricle with the electrode E8 being located near the top area of the ventricle and with electrode E1 being located near the bottom area of the ventricle, a depolarization wave front is created that will pass through the ventricle (whether the left or right ventricle) from top to bottom. Hence, by selectively controlling how the stimulation currents are applied to the multiple electrodes that are dispersed throughout a desired heart chamber(s), depolarization wave fronts may be evoked that cause the cardiac tissue to contract, and hence pump blood, in a manner that maximizes stroke volume and ejection fraction.

Figure 4:
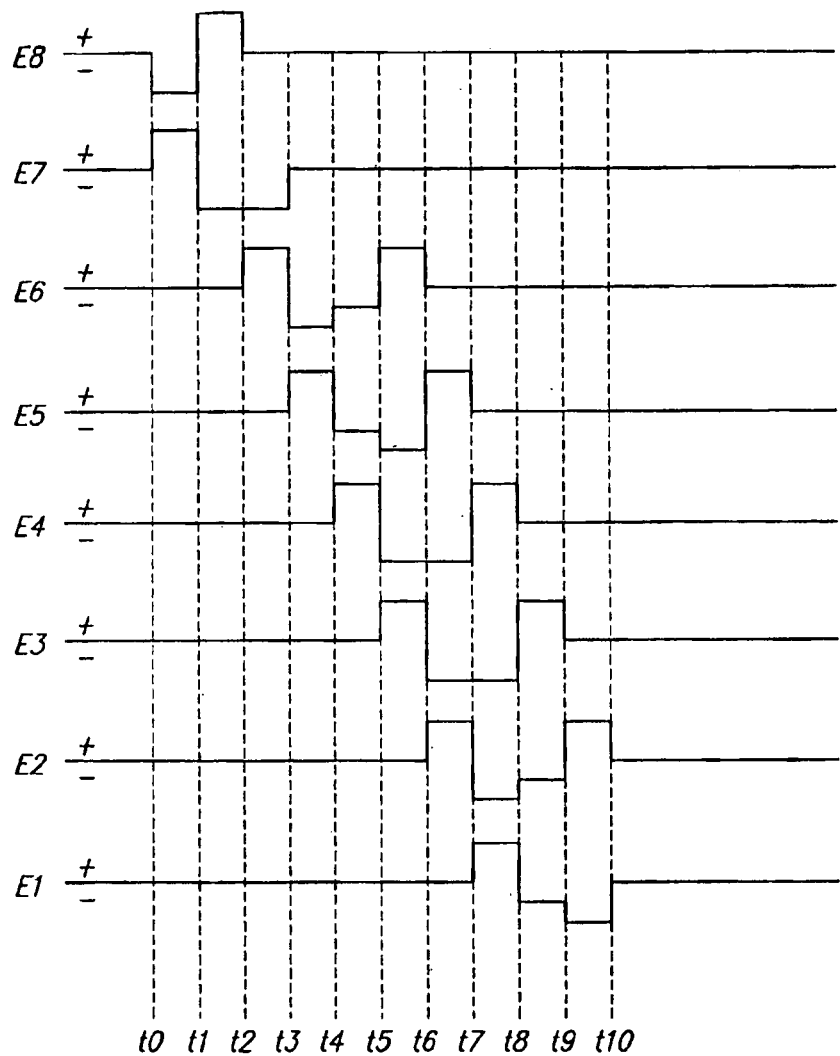

FIG. 4 depicts another timing diagram that illustrates a different way in which a depolarization wave front could be evoked through selective application of current pulses to the multiple electrodes E1-E8. As seen in FIG. 4, beginning at time t0 and continuing until time t1, a fixed current flows from electrode E7 to electrode E8. Beginning at time t1 and continuing until time t2, the polarity switches, and the fixed current flows from electrode E8 to electrode E7. Beginning at time t2, electrode E8 is turned off (i.e., no more current is sourced or sunk through such electrode). However, also beginning at time t2 and continuing until time t3, a fixed current flows from electrode E6 to electrode E7. Beginning at time t3 and continuing until time t4, a fixed current flows from E5 to E6.

Still with reference to FIG. 4, it is seen that beginning at time t4 and continuing until time t5, a fixed current flows from electrode E4 to both electrodes E5 and E6, with roughly ½ of the current flowing to electrode E5 and the other ½ flowing to electrode E6. (Other fractional current splits could also be programmed, e.g., ⅓ of the current may flow to E5, and ⅔ may flow to E6.) Beginning at time t5 and continuing until time t6, a fixed current flows from electrodes E3 and E6 to electrodes E5 and E4. That is, during this time (t5-t6), a current is being simultaneously sourced from electrodes E3 and E6 at the same time that the same current is being sunk through (returned through) electrodes E4 and E5. During the time period t6-t7, a current similarly flows from electrodes E5 and E2 to electrodes E4 and E3. During the time period t7-t8, a fixed current flows from electrodes E4 and E1 to electrodes E3 and E2. During the time period t8-t9, a fixed current flows from electrode E3 to both electrodes E2 and E1, with roughly ½ the current that is sourced from electrode E3 going to E2 and ½ going to E1. Finally, as the example in FIG. 4 indicates, during the time period t9-t10, a fixed current flows from electrode E2 to electrode E1. After time t10, all the electrodes are turned off.

Figure 5:
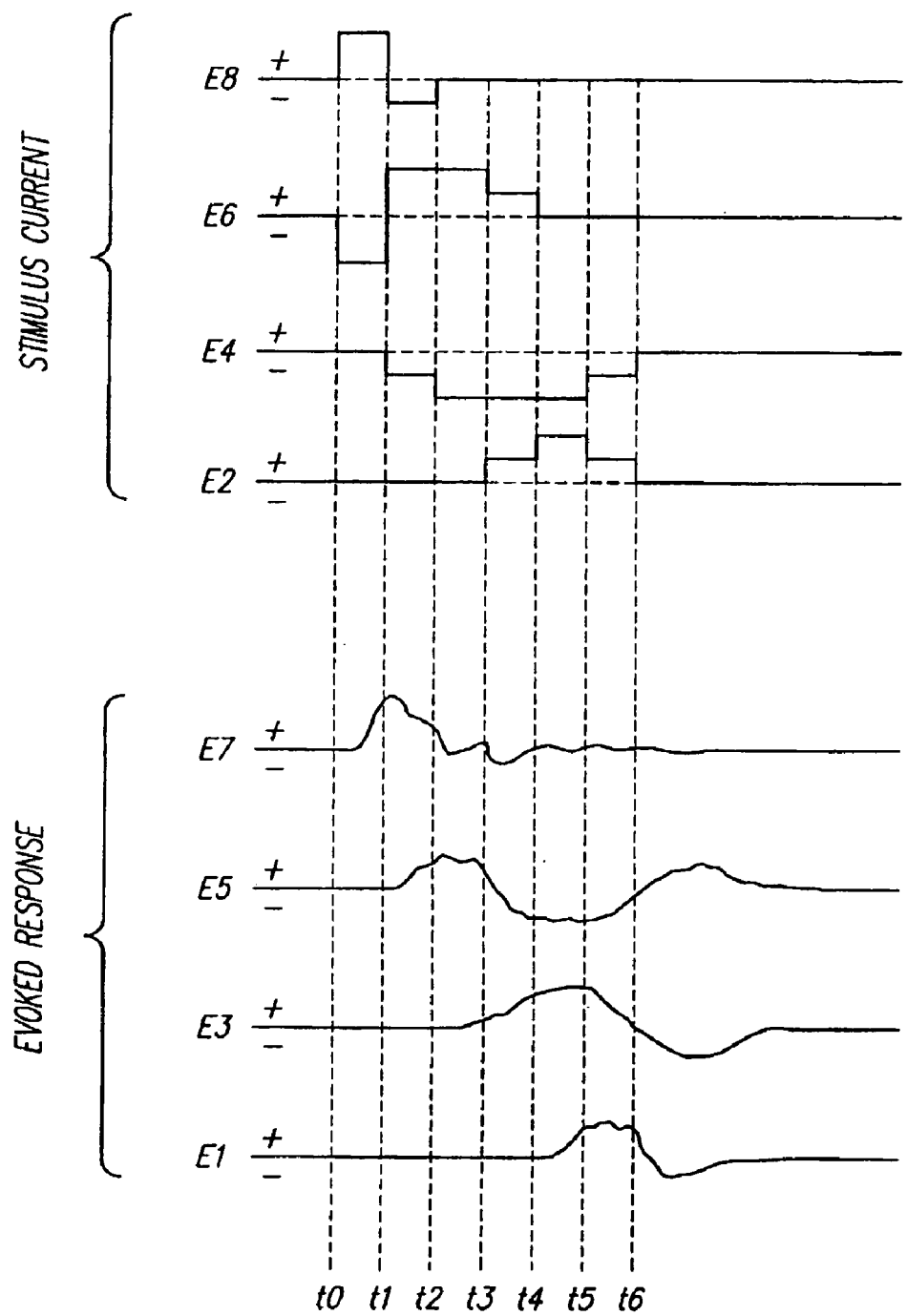

Not all of the electrodes need be used for stimulation. For example, as shown in the timing waveform diagram of FIG. 5, a current stimulus may be selectively applied through electrodes E2, E4, E6 and E8, while electrodes E1, E3, E5 and E7 are used for sensing. The example presented in FIG. 5 illustrates a current stimulus is first applied, during the time period t0-t1, to electrodes E6 and E8, with the current flowing from E8 to E6. (For purposes of FIG. 5, and the other timing diagrams presented herein, a positive current pulse shown by a given electrode indicates that the given electrode is sourcing or emitting current, whereas a negative current pulse indicates the given electrode is sinking or receiving current.) During the time period t1-t2, the same current continues to flow from E6, but only ½ flows to electrode E8, with the other ½ flowing to electrode E4. During the time period t2-t3, the same current continues to flow from E6, with all of the current flowing to E4. During the time period t3-t4, the same current continues to flow to (sink into) electrode E4, but only ½ is sourced from E6, with the other ½ being sourced from E2. During the time period t4-t5, the same current continues to flow to (sink into) electrode E4, and the entire current is sourced from electrode E2. During the time period t5-t6, the amount of current flowing from E2 to E4 is reduced by roughly ½; and after time t6 all the electrodes are turned off.

Also shown in FIG. 5 are representative depolarization signal waveforms of the type that may be sensed on the sensing electrodes E1, E3, E5, and E7 at the same time that current stimuli are being applied to the stimulating electrodes E2, E4, E6 and E8.

It should be appreciated, from the foregoing examples, that the possible combinations for stimulating with controlled electrical currents and sensing evoked or intrinsic depolarization using multiple electrodes within a given heart chamber(s) are endless. Advantageously, the controlled (or programmed) amplitudes of the stimulating currents (generated by the DAC current sources 20', shown, e.g., in FIG. 2) may be applied simultaneously to two or more of the multiple electrodes contained within the stimulation area or site. At any instant of time, however, the total amount of current must balance, i.e., the total current being sourced (emitted) from the implantable current sources, e.g., DAC current sources, should equal the total amount of current being sunk into (returning to) the implantable current sources. With current balancing being the only limitation, any number of electrodes may be used to source and sink current simultaneously. Through selective control of how the stimulating currents are applied, including their amplitude and timing, various depolarization wave fronts may be evoked within the desired heart chamber that assist the heart to be more efficient, e.g., by increasing stroke volume and/or by increasing the ejection fraction. Additionally, through the principle of superposition, resolution of the stimulation or sensing sites may be enhanced by sensing or stimulating on multiple electrodes to focus on a specific site.

Sensing of evoked responses, or intrinsic activity, may occur simultaneously (i.e., at the same time with, or within a few microseconds of) the application of stimulation currents. Such sensing may advantageously guide how the stimulation should be applied, or if it need be applied at all (demand stimulation—providing a current stimulus only if needed), so as to steer the depolarization wave front in a desired direction.

Thus, it is seen that the present invention provides an implantable stimulus device that both senses cardiac activity and stimulates the cardiac tissue from a multi-channel current-controlled pulse generator on demand as determined or steered by the cardiac activity that is sensed, and/or as programmed.

It is further seen that the invention provides a method of treating congestive heart failure using a multi-channel current-controlled pulse generator coupled to multiple stimulation sites in the left ventricle, or other chambers of the heart, for the purpose of assisting the heart to operate more efficiently, i.e., to improve stroke volume and increase the ejection fraction.

While the invention herein disclosed has been described by means of specific embodiments and applications thereof, numerous modifications and variations could be made thereto by those skilled in the art without departing from the scope of the invention set forth in the claims.

What is claimed is:

1. A method comprising:
   providing at least two implantable electrostimulation electrodes in contact with cardiac tissue, the at least two implantable electrostimulation electrodes electrically coupled to a current-controlled implantable pulse generator;
   generating a wireless control signal to control sourcing, or sinking, of an electrostimulation current, the wireless control signal generated using an implantable controller separate and distinct from (1) the electrostimulation electrodes and (2) the current-controlled implantable pulse generator, and the implantable controller wirelessly coupled to the current-controlled pulse generator;
   sourcing a current to one or more implantable electrostimulation electrodes in response to the received wireless control signal;
   sinking a current from one or more implantable electrostimulation electrodes in response to the received wireless control signal; and
   instantaneously balancing the total current sourced with a total current sunk concurrently.

2. The method of claim 1, comprising:
   instantaneously balancing, across multiple current-controlled implantable pulse generators, the total current sourced with the total current sunk concurrently.

3. The method of claim 1, comprising at least one of:
   (1) sourcing the current to one or more implantable electrostimulation electrodes, the current sourced corresponding to a digital representation of a specified source current value, in response to the wireless control signal; or
   (2) sinking the current from one or more implantable electrostimulation electrodes, the current sunk corresponding to a digital representation of a specified sink current value, in response to the wireless control signal.

4. The method of claim 3, comprising:
   sensing a signal corresponding to at least one of: (1) intrinsic cardiac activity, (2) an evoked response, or (3) a direction in which a depolarization wave front is moving through cardiac tissue; and
   controlling at least one of: (1) a timing, (2) a duration, (3) a polarity, or (4) a magnitude, of an electrostimulation current, in a manner that tends to control the direction in which a depolarization wave front is moving through cardiac tissue, using information derived from the sensing.

5. The method of claim 1, comprising controlling at least one of: (1) a timing, (2) a duration, (3) a polarity, or (4) a magnitude, of an electrostimulation current, in a manner that tends to increase at least one of: (1) stroke volume, or (2) ejection fraction.

6. The method of claim 1, comprising:
   providing at least two sensing electrodes in contact with cardiac tissue; and
   amplifying a signal corresponding to at least one of: (1) intrinsic cardiac activity, (2) an evoked response, or (3) a direction in which a depolarization wave front is moving through cardiac tissue.

7. The method of claim 6, comprising assigning an electrostimulation electrode as a sensing electrode.

8. The method of claim 1, wherein the current-controlled implantable pulse generator includes the implantable electrostimulation electrodes.

* * * * *